(12) United States Patent
Park (10) Patent No.: US 9,901,335 B2
(45) Date of Patent: Feb. 27, 2018

(54) METHOD AND APPARATUS FOR SECURING SOFT TISSUE TO BONE

(71) Applicant: Maxwell Choongwon Park, Calabasas, CA (US)

(72) Inventor: Maxwell Choongwon Park, Calabasas, CA (US)

(*) Notice: Subject to any disclaimer, the term of this patent is extended or adjusted under 35 U.S.C. 154(b) by 337 days.

(21) Appl. No.: 14/327,574

(22) Filed: Jul. 10, 2014

(65) Prior Publication Data
US 2016/0007994 A1 Jan. 14, 2016

(51) Int. Cl.
*A61B 17/04* (2006.01)
*A61F 2/08* (2006.01)

(52) U.S. Cl.
CPC ........ *A61B 17/0401* (2013.01); *A61F 2/0805* (2013.01); *A61B 2017/0409* (2013.01); *A61B 2017/0414* (2013.01); *A61B 2017/0435* (2013.01); *A61B 2017/0445* (2013.01); *A61B 2017/0453* (2013.01)

(58) Field of Classification Search
CPC ... A61B 17/0401; A61B 17/08; A61B 17/083; A61B 17/12; A61B 17/122; A61B 2017/1125; A61B 2017/12004; A61B 2017/1225; A61B 2017/1227
See application file for complete search history.

(56) References Cited

U.S. PATENT DOCUMENTS

| | | | |
|---|---|---|---|
| 2,467,864 A | 4/1949 | Sisk | |
| 2,616,328 A | 11/1952 | Kingsmore | |
| 3,832,931 A | 9/1974 | Talan | |
| 3,859,874 A * | 1/1975 | Joeckel | B25B 7/123 81/367 |
| 3,902,614 A * | 9/1975 | Roberts | B66C 3/16 294/106 |
| 3,981,308 A * | 9/1976 | Schlein | A61B 17/2804 606/205 |
| 5,142,776 A * | 9/1992 | Neely | B25B 5/06 24/509 |
| D346,862 S * | 5/1994 | Koros | D24/143 |
| 5,501,126 A * | 3/1996 | Wright | B25B 7/00 81/302 |
| 5,618,261 A * | 4/1997 | Nevyas | A61B 17/0231 600/236 |
| 5,720,751 A * | 2/1998 | Jackson | A61B 17/7032 606/104 |
| 5,726,370 A * | 3/1998 | Yanagisawa | G10D 13/006 84/422.1 |
| 5,776,147 A * | 7/1998 | Dolendo | A61B 17/122 606/142 |

(Continued)

*Primary Examiner* — Dianne Dornbusch (57) ABSTRACT

An apparatus and method for affixing soft tissue to bone is provided. The apparatus comprises first and second arms including first and second jaws on distal ends. The second arm is mated to the first arm at a hinge located between the proximal ends of the first and second arms and distal ends of the first and second arms. To enter into an engaged position, the first and second arms pivot around the hinge such that the distal ends of the first and second arms close towards one another, and the proximal ends of the first and second arms move apart from one another. The engaged position causes the first jaw on the distal end of the first arm and the second jaw on the distal end of the second arm to compress and hold soft tissue.

12 Claims, 5 Drawing Sheets

(56) References Cited

U.S. PATENT DOCUMENTS

| | | | |
|---|---|---|---|
| 5,827,263 A * | 10/1998 | Furnish | A61B 17/2909 606/1 |
| 6,000,686 A * | 12/1999 | Yates | B25B 5/12 269/143 |
| 6,283,913 B1 * | 9/2001 | Seibel | A61B 1/32 600/219 |
| 6,540,770 B1 | 4/2003 | Tornier et al. | |
| 7,588,585 B2 * | 9/2009 | Gold | A61B 17/122 606/206 |
| 7,637,405 B2 * | 12/2009 | Emmerling | B60R 9/055 224/319 |
| 7,785,357 B2 | 8/2010 | Guan et al. | |
| 7,833,255 B2 | 11/2010 | Chow et al. | |
| 8,007,435 B2 * | 8/2011 | Hartnick | A61B 17/0206 128/200.26 |
| 8,349,010 B2 | 1/2013 | Justin et al. | |
| 8,409,229 B2 * | 4/2013 | Wiedenbein | A61B 17/122 606/158 |
| 8,523,902 B2 | 9/2013 | Heaven et al. | |
| 8,574,275 B2 | 11/2013 | Stone et al. | |
| 8,652,208 B2 | 2/2014 | Kovalski | |
| 8,747,469 B2 | 6/2014 | Wang et al. | |
| 8,845,725 B2 | 9/2014 | Barwood et al. | |
| 9,005,246 B2 | 4/2015 | Burkhart et al. | |
| 9,101,462 B2 | 8/2015 | Miller | |
| 9,241,783 B2 | 1/2016 | Trenhaile et al. | |
| 2001/0034536 A1 * | 10/2001 | Looper | A61B 17/122 606/205 |
| 2001/0049540 A1 * | 12/2001 | Santilli | A61B 17/128 606/158 |
| 2003/0005798 A1 * | 1/2003 | Kuchar | B25B 7/02 81/426 |
| 2005/0204874 A1 * | 9/2005 | Chen Cheng | B25B 7/123 81/369 |
| 2008/0275554 A1 | 11/2008 | Iannarone et al. | |
| 2009/0223331 A1 * | 9/2009 | Jordan | B25B 7/02 81/371 |
| 2011/0087326 A1 | 4/2011 | Paulos | |
| 2011/0112550 A1 | 5/2011 | Heaven et al. | |
| 2011/0112558 A1 | 5/2011 | Whayne et al. | |
| 2012/0143269 A1 * | 6/2012 | Ichelmann | A61B 17/7082 606/86 R |
| 2012/0245686 A1 | 9/2012 | Park | |
| 2013/0331942 A1 | 12/2013 | Baird | |
| 2014/0046369 A1 | 2/2014 | Heaven et al. | |
| 2015/0167707 A1 * | 6/2015 | Hyers | F16B 2/10 24/488 |

* cited by examiner

METHOD AND APPARATUS FOR SECURING SOFT TISSUE TO BONE

BACKGROUND

The present disclosure generally relates to orthopaedic surgery, and more specifically, to an apparatus and procedure for advancing soft tissue into a bony tunnel.

When soft tissue such as tendons or ligaments becomes detached from bone, joints may be rendered non-functional. For example, tendon detachment may cause potential motor deficits and weakness, while ligament detachment may cause instabilities. In order to restore optimal functionality, soft tissue must be reattached to bone. Thus, a variety of different devices and procedures have been developed for reattaching soft tissue to bone.

SUMMARY

The disclosed subject matter relates to an apparatus for affixing soft tissue to bone. The apparatus comprises a first arm including a first jaw on a distal end of the first arm, and a second arm mated to the first arm at a hinge. The second arm also includes a second jaw on a distal end of the second arm. The hinge is located between the proximal ends of the first and second arms and distal ends of the first and second arms. To enter into an engaged position, the first and second arms pivot around the hinge such that the distal ends of the first and second arms close towards one another, and the proximal ends of the first and second arms move apart from one another. The engaged position causes the first jaw on the distal end of the first arm and the second jaw on the distal end of the second arm to compress and hold soft tissue.

According to various aspects of the subject technology, a system for affixing soft tissue to bone is provided. The system includes a clamp and an applicator. The clamp includes a first arm comprising a first jaw on a distal end of the first arm, a threaded socket for insertion of a screw, and a set of mating grooves on a proximal end of the first arm. The clamp further includes a second arm mated to the first arm at a hinge. The second arm comprises a second jaw on a distal end of the second arm. The hinge is located between the proximal ends of the first and second arms and distal ends of the first and second arms. When the screw is advanced into the threaded socket, a pressure is applied by the screw onto a lever in the second arm causing the first arm and second arm to progressively pivot around the hinge and advance to an engaged position where the distal ends of the first and second arms close towards one another and the proximal ends of the first and second arms move apart from one another. The system further includes a driver. The driver comprises a knob operable by a user and a driver shaft attached to the knob. The driver shaft provides for an application, by the user, of a torque from the driver to the screw insertable into the threaded socket. The system also includes an applicator comprising a proximal handle and a cannulated shaft connected to the handle on the proximal end of the cannulated shaft. The cannulated shaft includes a tip configured to mate to the first arm by attaching to the set of mating grooves on the proximal end of the first arm. The cannulated shaft further includes a cannulation through which the driver passes.

The disclosed subject matter also relates to a method for affixing soft tissue to bone. The method comprises inserting a clamp and the soft tissue into an aperture in the surface of a bone structure, where the soft tissue is interposed between the clamp. The clamp includes a first arm comprising a first jaw on a distal end of the first arm and a threaded socket for insertion of a screw. The clamp further includes a second arm mated to the first arm at a hinge. The second arm comprises a second jaw on a distal end of the second arm. The hinge is located between the proximal ends of the first and second arms and distal ends of the first and second arms. When the screw is advanced into the threaded socket, a pressure is applied by the screw onto a lever in the second arm causing the first arm and second arm to progressively pivot around the hinge and advance to an engaged position where the distal ends of the first and second arms close towards one another and the proximal ends of the first and second arms move apart from one another. The method further comprises advancing a screw, with a driver, into the threaded socket to cause the clamp to transition to the engaged position. The first jaw on the distal end of the first arm and the second jaw on the distal end of the second arm progressively compress and hold the soft tissue when the clamp is transitioned to the engaged position.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

Certain features of the subject technology are set forth in the appended claims. However, for purpose of explanation, several embodiments of the subject technology are set forth in the following figures.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. This description includes specific details for the purpose of providing a thorough understanding of the subject technology. However, the subject technology is not limited to the specific details set forth herein and may be practiced without these specific details.

The disclosed subject matter relates to an apparatus for affixing soft tissue to bone. The apparatus comprises a first arm including a first jaw on a distal end of the first arm, and a second arm mated to the first arm at a hinge. The second arm also includes a second jaw on a distal end of the second arm. The hinge is located between the proximal ends of the first and second arms and distal ends of the first and second arms. To enter into an engaged position, the first and second arms pivot around the hinge such that the distal ends of the first and second arms close towards one another, and the proximal ends of the first and second arms move apart from one another. The engaged position causes the first jaw on the distal end of the first arm and the second jaw on the distal end of the second arm to compress and hold soft tissue.

There are at least two types of bony sockets or tunnels to which soft tissue may be affixed, the first being a circumferential bone with a certain density, and the second being relatively hollow bone. A socket has only one aperture and a tunnel has two apertures, one at each end of the tunnel. While both types of sockets or tunnels have a surface cortical bone, circumferential bone has deeper metaphyseal bone with varying degrees of density. Cortical bone is the hardest, densest bone, and is the optimal bone for achieving implant fixation. Thus, a soft tissue fixation device that relies on cortical bone would be considered relatively ideal. There is also a preference for advancing soft tissue into bone without externalizing the soft tissue when certain soft tissue is involved. For example, externalizing soft tissue such as the proximal biceps tendon in the human shoulder requires potentially more dissection and surgical time, both of which should be minimized if possible so as to reduce post-surgical pain and intra-operative risks (e.g. anesthesia risks).

The currently disclosed soft tissue fixation device fixates soft tissue directly, then allows for fixation through a bony hole or aperture that leads into a tunnel, socket, or void. Thus, the device does not primarily rely on interference fixation alone (e.g. with a screw, or similar implant that fills a bony tunnel with soft tissue interposed between the implant and bone, metaphyseal and or cortical). The claimed device, however, does not preclude subsequent fixation that relies on interference or other manners of fixation. For example, it the device were to be placed entirely below the cortical bone, a standard interference screw could still be advanced over the device, with the soft tissue of interest achieving interference fixation between the screw and any adjacent bone.

The device described herein provides for direct soft tissue fixation (as the device itself fixates to soft tissue) and subsequent bony fixation (as the device engages bone) using the features of the described device and applicator with driver, as described in detail below. The device also provides for fixation in all types of bone, hollow or otherwise, and in two ways, open and arthroscopic. Notably, while there may exist implants that primarily, and in some cases solely, rely on interference fixation of soft tissue between two surfaces, implant and bone (versus direct fixation between implant and soft tissue), the device described herein relies also on interference fixation insofar as the device provides frictional resistance of any soft tissue of interest between the device and adjacent bone.

Figure 1:
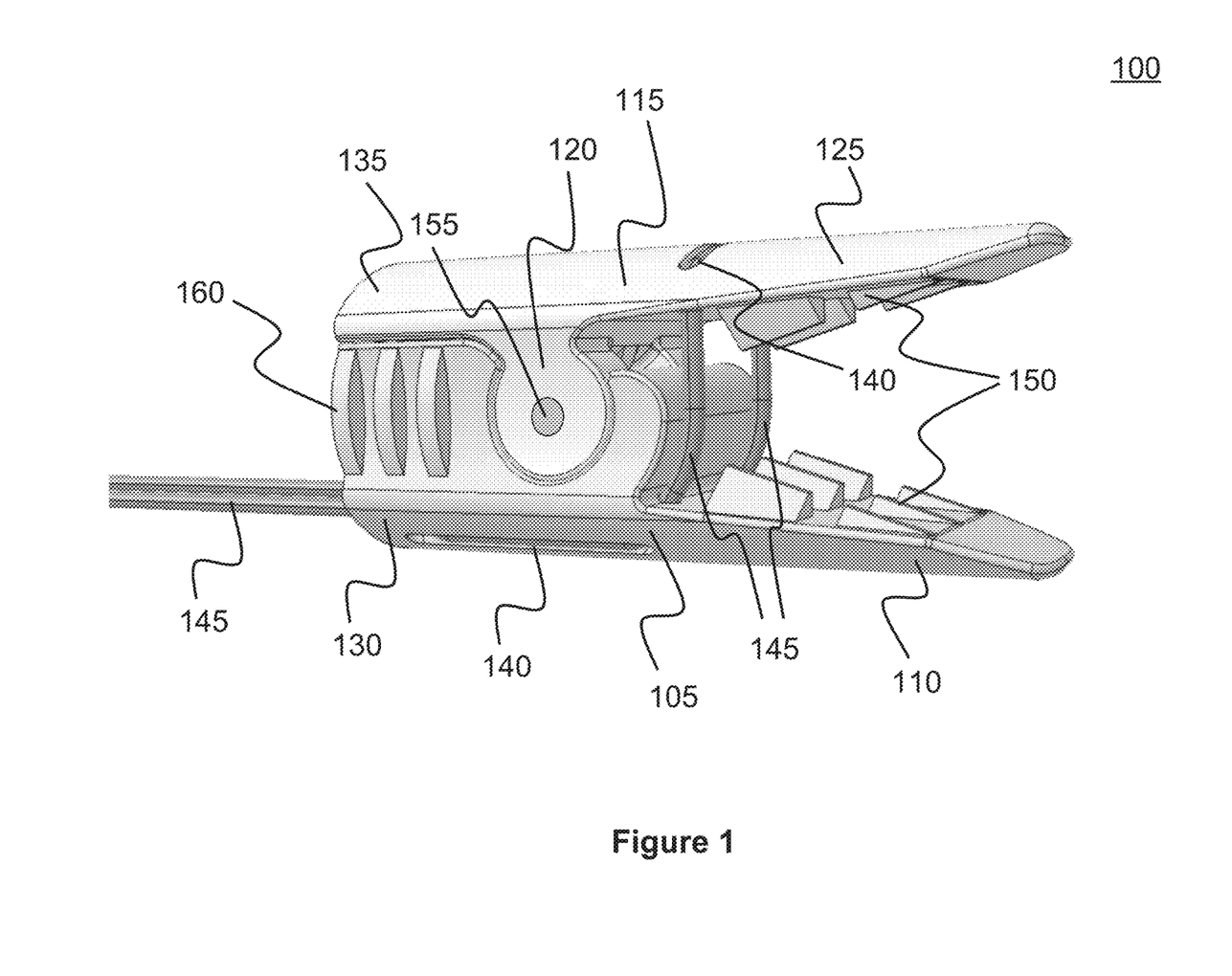
FIG. 1 provides a side perspective view graphical representation of an implantable soft tissue fixation device.

FIG. 1 provides a side perspective view graphical representation of an implantable soft tissue fixation device. The soft tissue fixation device 100 takes a shape that resembles a clamp. A first arm 105 of the device includes a first jaw 110 on a distal end of the first arm 105. A second arm 115 is mated to the first arm at a hinge 120, and the second arm 115 includes a second jaw 125 on a distal end of the second arm. The hinge 120 is located between the distal ends of the first arm 105 and second arm 115 and a first proximal end 130 of the first arm and a second proximal end 135 of the second arm, respectively. The hinge 120 provides a point around which the first arm 105 and second arm 115 may pivot. Additionally, the hinge may include a tunnel 155 that passes from one side of the hinge through to the opposite side. This tunnel allows for the passage of a suture such that the soft tissue fixation device may be securely held to an applicator, as further described in FIG. 4 below. The soft tissue fixation device, as illustrated in FIG. 1, is in an unengaged position. This is shown by the first jaw 110 and second jaw 125 remaining in an open position.

While the hinge may take on any one of multiple configurations to enable a hinge mechanism, a hinge that limits the material for the device would be relatively ideal from a mechanical standpoint so as to limit the number of material and mechanical interfaces exposed to potential failure. For example, a hinge between the first and second arms could be created without additional material beyond a simple mating between the first and second arms. For example, the first arm could slide into a matable slot of the second arm in a direction that is orthogonal to the long axis of the device, or as another example the hinge could be configured to snap together.

In order to enter into an engaged position, the first arm 105 and second arm 115 pivot around the hinge 120 such that the distal ends of the first and second arms close towards one another. At the same time, the proximal ends of the first arm and second arm move apart from one another. By advancing into an engaged position, the first jaw on the distal end of the first arm and the second jaw on the distal end of the second arm can compress and hold soft tissue, as will be shown in FIGS. 5A-5C.

In some embodiments, each of the first and second arms may include a set of channels 140. The channels provide a passage for durable sutures 145. When the suture passing through the channels is cinched with a certain tension, the soft tissue fixation device can be transitioned to an engaged position. And when the free ends are tied off to one another, the soft tissue fixation device can be held and maintained in an engaged position, with the soft tissue of interest interposed between the first and second arms. The suture that passes through the channels, and between each of the two arms, should be distal to the hinge center of rotation to initiate the movement of the arms to an engaged position. This does not preclude the creation of other channels within the device at any location relative to the hinge, proximal or distal. Sutures passing through the device through channels can be used for fixation of additional soft tissue after the device is secured to its intended location within bone. Additionally, in some embodiments, at least one of the first jaw and the second jaw may include a set of horizontal teeth and/or a set of vertical teeth 150, that may or may not interdigitate. The teeth provide extra grip to the first and second jaws, thereby providing a more secure hold on the soft tissue interposed between the first and second arms. The teeth effectively increase the contact area between the soft tissue of interest and the first and second jaws, increasing the frictional resistance to soft tissue slippage and failure when a stress or load is applied. These teeth 150 or protrusions may take any number of cross-sectional geometries and configurations (e.g. beveled, serrated, needle-like, tapered) in order to optimize contact with the soft tissue of interest.

Further increasing the contact area between soft tissue and the implantable soft tissue fixation device are additional teeth or ridges 160 at the proximal end of the first arm 105. These additional teeth or ridges 160 provide frictional resistance between the soft tissue fixation device and any soft tissue of interest when the device is inserted through an aperture in cortical bone, as will be described in further details in FIGS. 3 and 5A-5C. The soft tissue of interest will experience interference fixation between the device and adjacent bone. Notably, a ridge, or any number of ridges, may be disposed circumferentially about the entire proximal aspect of the device (not depicted). A ridge or ridges on the device, orthogonal to the ridges 160 depicted (on the sides of the device where ridges 160 are not depicted), could serve to engage cortical bone should the operator choose not to place the device completely beneath the cortical bone. With the proximal aspect of the device (proximal to the hinge center of rotation) flush to the surface of the cortical bone or proud, the ridge or ridges (not depicted) could be configured to increase contact with the adjacent bone once the device is in the engaged position, thereby increasing the resistance to device pull-out failure from the bone. A ridge is not necessarily a protrusion of implant material, but in effect could also be made by creating cutout notches (using less material). The notch or notches could be configured to engage adjacent bone such that any device material proximal to the notch cutout could overhang the surface aperture cortical bone with a lip of device material. This might be one of many scenarios where the soft tissue fixation device is slightly proud in an engaged position relative to the surface cortical bone. One advantage of such a lip of device material that overhangs the surface cortical bone is that the device could be well maintained at a fixed depth within the socket or tunnel of interest. In other words, the lip would act as a mechanical stopper against device insertion beyond a certain depth.

Figure 2:
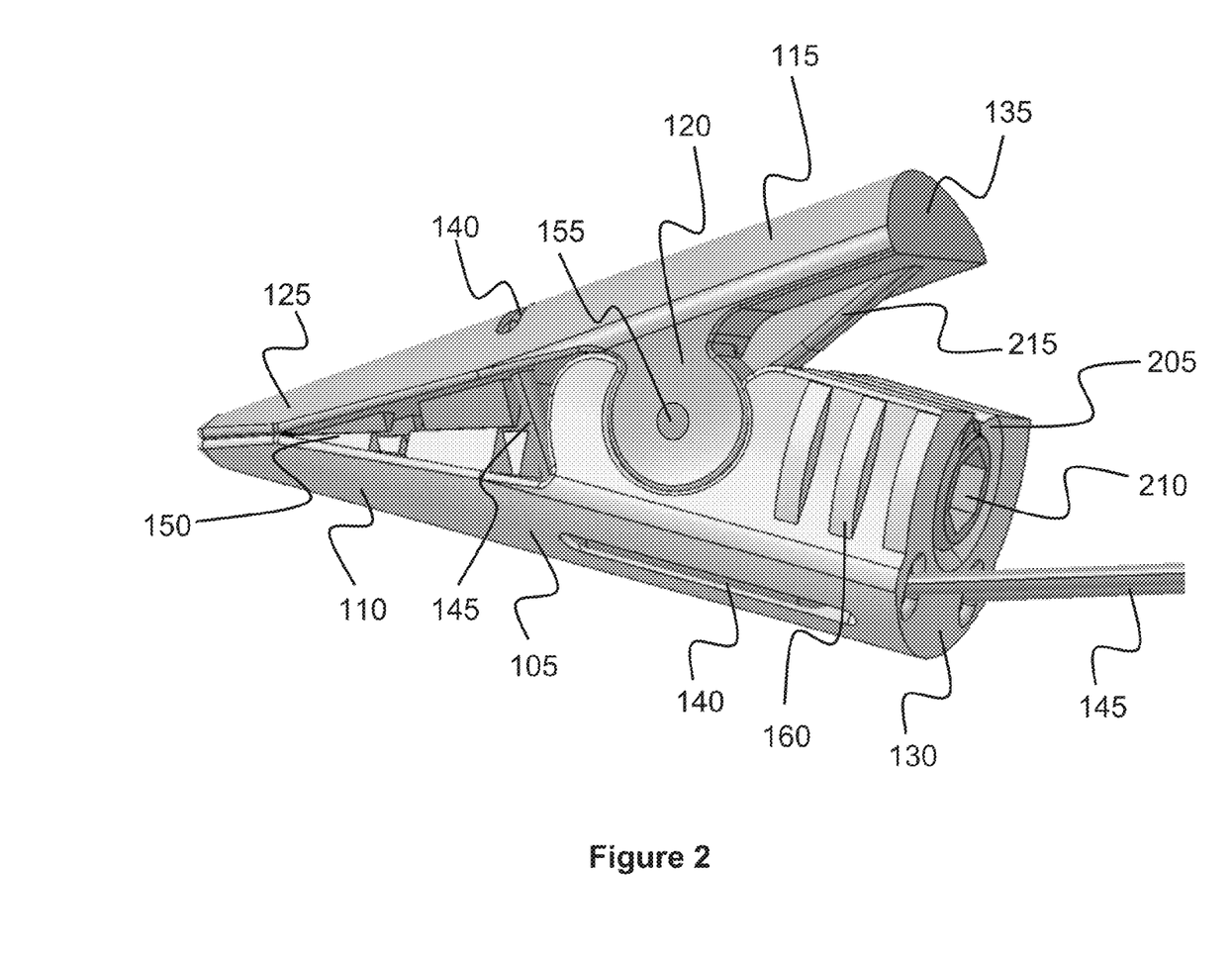
FIG. 2 provides an angled view graphical representation of the implantable soft tissue fixation device in an engaged position.

FIG. 2 provides an angled view graphical representation of the implantable soft tissue fixation device in an engaged position. As described above in reference to FIG. 1, the soft tissue fixation device includes a first arm 105 with a first jaw 110 on a distal end of the first arm 105. The soft tissue fixation device further includes a second arm 115 that is mated to the first arm at a hinge 120. The second arm 115 also includes a second jaw 125 on a distal end of the second arm. The hinge 120, located between the proximal ends and the distal ends of the first and second arms, provides a point around which the first arm 105 and second arm 115 may pivot. The hinge may include a tunnel 155 that passes from one side of the hinge through to the opposite side, thereby allowing for the passage of a suture. The edges of this tunnel may be rounded to limit suture damage should any suture be tensioned within the tunnel.

In this figure, the first and second arm of the soft tissue fixation device is pivoted around the hinge into a fully engaged position. That is, the first jaw on the distal end of the first arm and the second jaw on the distal end of the second arm are in closer proximity to one another to compress and hold soft tissue (not shown) interposed between the first and second jaws. The teeth or ridges 150, 160 increase frictional resistance to soft tissue slippage, elongation, and failure by increasing contact area between the implantable soft tissue fixation device and the soft tissue of interest. Teeth 150 increase contact area between soft tissue and device, and help fixate soft tissue directly with the device in an engaged position, while ridges 160 increase contact area between soft tissue and implant to increase frictional resistance to pull-out failure of soft tissue interposed between the device and bone.

The soft tissue fixation device shown in FIG. 2 further includes a threaded socket 205 for insertion of a screw 210. The screw, when advanced into the threaded socket, applies a pressure on a lever 215 on the second arm to cause the second arm to progressively pivot around the hinge and advance the first and second arms into the engaged position. In other words, the first and second arms pivot around the hinge such that the distal ends of the first and second arms close towards one another, and, at the same time, the proximal ends of the first and second arms move apart from one another. The deeper the screw is advanced into the socket, the more the second arm pivots around the hinge to cause the distal ends of the first and second arms to close towards one another. Accordingly, the advancement of the screw can be adjusted to accommodate different amounts of soft tissue that is to be compressed and held by the first and second jaws. Also, the advancement of the screw can be adjusted to accommodate the dimensions of the surrounding bone that the soft tissue fixation device encounters during a given procedure.

In an alternate embodiment, the screw may not be necessary to advance the device to the engaged position. For example, the driver itself could be threaded at its distal tip to function as a screw would, and as another example, a non-threaded tool or peg could be advanced into the socket in order to create a force against a lever, thus progressively causing the distal end of the first and second arms to close towards one another.

It is noted that when the soft tissue fixation device is in the fully engaged position, the first and second proximal ends 130 and 135 are more spread out than when the device is in the unengaged position. As will be shown in more detail in FIG. 3 and FIG. 5C, the spreading out of the proximal ends ultimately provides an anchor against the underside of cortical bone through which the device is inserted (the dimension of the device when in its engaged position is larger than the dimension of the drilled, reamed, or punched out cortical bone aperture). Further, a resistive anchoring force is provided by any tension that may be encountered by the attached soft tissue.

Notably, the soft tissue fixation device may not need to be wholly on the underside of cortical bone. In other words, the device, prior to creating the engaged position, may be applied so that the proximal ends of the first and second arms (proximal to the hinge center of rotation) are contained within the cortical bone at the aperture of the bony tunnel or socket, flush or slightly proud relative to the surface of the cortical bone aperture. Once the proximal aspect of the device (that aspect proximal to the hinge center of rotation) is contained within the cortical bone, the screw may be advanced so that the proximal ends of the first and second arms spread out until contact is made with the cortical bone of the aperture, thus fixating the soft tissue of interest into a bony socket or tunnel. In this scenario, direct fixation to bone is created between the device and bone, and interference fixation is created as the soft tissue is held tightly between the device and adjacent bone. The interference fixation will be variable depending on the type of bone encountered. Metaphyseal (non-hollow bone) versus diaphyseal (relatively hollow bone) will provide variable fixation strengths. For both types of bone, interference fixation is provided by cortical bone.

Figure 3:
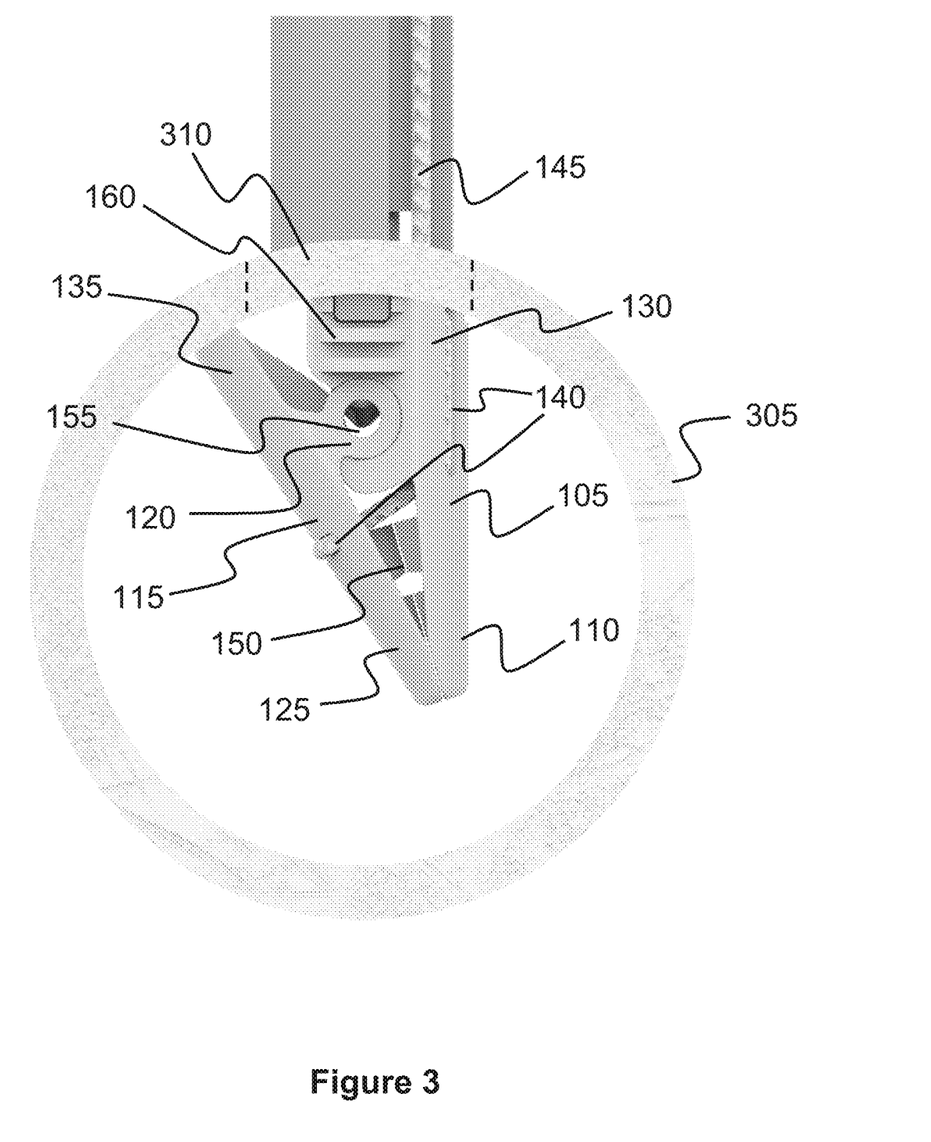
FIG. 3 provides a graphical representation of the implantable soft tissue fixation device in an engaged position anchored against bone.

In some embodiments, the first and second arms may include a set of channels 140 that provide a passage for durable sutures 145. The sutures, when passed through the channels, cinched, and tied off, provide an extra mechanism of securing the soft tissue fixation device in the engaged position beyond the screw element. As shown in FIG. 3, the sutures may be cinched and tied off at the proximal end of the first arm where the sutures exit the channels of the first arm. Once tied off or secured to one another, the sutures will prevent the first and second arm from pivoting in a direction where the first and second jaws at the distal ends of the arms come apart. The sutures should pass between the first and second arms distal to the hinge center of rotation before they are secured to one another. Furthermore, as discussed in reference to FIG. 1, at least one of the first jaw and the second jaw may include a set of horizontal teeth and/or a set of vertical teeth to provide extra grip and frictional resistance for holding the soft tissue interposed between the first and second arms. The teeth may be in a relatively angled orientation as well. Additionally, teeth or ridges at the proximal aspect of the first and second arms, proximal to, and/or including, the hinge element itself, provide additional frictional resistance to pull-out stress of the soft tissue, interposed between the device and any adjacent bone. These teeth or ridges may take on any number of configurations, ideally oriented to resist the direction of soft tissue slippage. Therefore, these teeth or ridges may be oriented in opposite directions if placed on opposite sides of the soft tissue fixation device.

In some embodiments, an eyelet or hole cutout may be provided on the distal end of either of the two arms (not shown in FIG. 1 or 2). This eyelet allows extra sutures from another source, whether from free sutures or other implants, to be managed in a controlled manner. For example, if desired, this would allow sutures to be passed, in either direction, through the center of the socket along the long axis of the device in a predictable, reproducible manner. Further, a notch at the distal edge of either or both arms could be configured and would function like an eyelet or hole cutout in managing and controlling any extra sutures. The surfaces of the eyelet or notch could be smooth to limit damage to any sutures. Prior to placing the device to bone, suture ends (e.g. free or looped) may be passed through an eyelet (in any direction) and in between the distal end of either of the first jaw 110 or second jaw 125. The sutures may be variably tensioned prior to screw 210 advancement. With screw advancement, whether or not the sutures are passed through the socket, the sutures would be fixated by the clamp between the first jaw 110 and second jaw 125 in the fully engaged position at the distal end of the device. Distal end of the device here would mean that region of the device distal to the hinge. The extra sutures can therefore be fixated in place at the location of the aperture. If the sutures of interest were passed through the socket (whether or not being passed through an eyelet or hole cutout, or by a notch), the screw could provide interference fixation for the sutures secured between the screw threads and the matable thread grooves in the socket.

In some embodiments, the screw 210 and socket 205 may further be configured to engage extra sutures from another source. This may be accomplished by placing free ends or a looped end of the extra sutures through the socket 205 prior to inserting the device into bone. The extra sutures can be passed through the socket 205 in a distal to proximal direction, or a proximal to distal direction. Once the device is placed to the desired position within the bone the extra sutures may be variably tensioned. When the screw 210 is inserted and advanced into the socket 205, the sutures are securely fixed in place at the location of the aperture, fixated between the screw threads and the matable thread grooves of the socket.

FIG. 3 provides a graphical representation of the implantable soft tissue fixation device in an engaged position anchored against cortical bone. FIG. 3 provides a cross-sectional view of the cortical bone 305, and the aperture 310 dimension through which the soft tissue fixation device is inserted is represented in FIG. 3 by the dashed lines. The aperture may be a hole drilled, reamed, or punched out through the surface of cortical bone and provides a passage into the bone where the soft tissue fixation device may be secured. In general, diaphyseal bone has cellular elements deep to the cortical bone without much if any bony structural density, while metaphyseal bone has relatively more bony structural density deep to the cortical bone. Cortical bone has the most density, and thus provides an optimal structure to which the soft tissue fixation device may be anchored or secured.

The soft tissue fixation device in an unengaged position is first inserted through an aperture 310 in the cortical bone 305. When the device is in an unengaged position, the outer surface of the first arm is substantially parallel to an outer surface of the second arm, thereby providing a slimmer profile for which the device may pass through an aperture. In order for the soft tissue fixation device to operate properly, the aperture must be of a size large enough for the device to pass through in the unengaged position, but small enough such that the device cannot back out through the aperture in the engaged position. For example, the diameter of a circular aperture may be 1-2 mm larger than the profile of the soft tissue fixation device from the perspective of an insertion.

Once inserted, the soft tissue fixation device may be entered into the engaged position, for example, by advancing a screw into the proximal end of the first arm as discussed above in reference to FIG. 2. The device may further be secured in the engaged position by passing a suture 145 through channels 140 in the first and second arms, and cinching and tying the sutures off. For this purpose, the passage of sutures between the first and second arms should be distal to the center of rotation of the hinge mechanism. Notably, even without advancement of the screw 210, this suture mechanism would be sufficient to advance the device to an engaged configuration, and maintain this configuration.

In the engaged position, the outer surface of the first arm is at an angle to the outer surface of the second arm, as shown in FIG. 3. Once the soft tissue fixation device is in the engaged position, the proximal ends of at least one of the first arm and second arm provides an anchor against a backside of the aperture. In this example, the second proximal end 135 of the second arm 115 is in contact with the underside of the cortical bone 305. The anchoring force on the proximal ends of the first and second arms against the backside of the aperture of the cortical bone can be provided by any tension force of the soft tissue. The soft tissue (not depicted) is held by the first and second jaws, creating compression and frictional forces against the soft tissue. These frictional forces are not only enhanced within the jaws, but may further be enhanced along the sides of the device where additional ridges (for example, ridges 160) may be configured. This anchoring of the soft tissue fixation device is discussed in further detail in FIG. 5C.

As discussed above in reference to FIG. 2, the soft tissue fixation device may not need to be wholly inserted through the cortical bone. The device may be applied so that the proximal ends (that aspect which is proximal to the hinge center of rotation) of the first and second arms are flush or proud relative to the surface of the cortical bone aperture. Once the device is contained within the cortical bone to the appropriate depth, the screw may be advanced so that the proximal ends of the first and second arms spread out until contact is made with the cortical bone of the aperture, thus fixating the device directly to bone and the soft tissue of interest into a bony socket or tunnel. In this scenario, direct fixation to bone is created between the device and bone, and interference fixation is created as the soft tissue is held securely between the device and adjacent bone.

Figure 4:
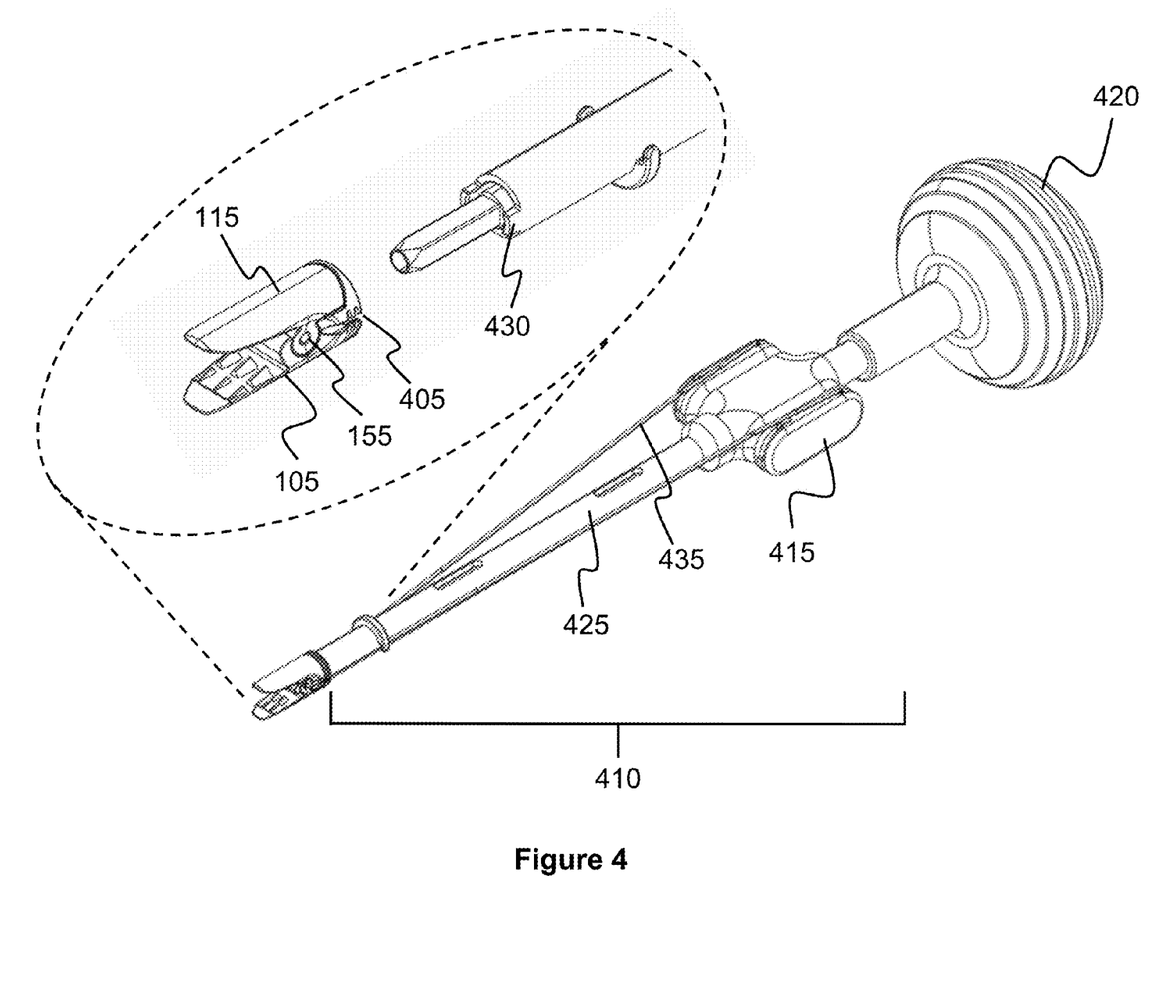
FIG. 4 illustrates an example of the implantable soft tissue fixation device mated to an applicator.

FIG. 4 illustrates an example of the implantable soft tissue fixation device mated to an applicator with a knob. The implantable device includes a first arm 105 and a second arm 115 that are utilized in securing soft tissue to bone. The first arm further includes a set of grooves 405 on the proximal end for mating to an applicator 410.

The applicator shown in FIG. 4 comprises a proximal handle 415. The applicator further comprises a cannulated shaft 425 connected to the handle 415 on the proximal end. The cannulated shaft includes a tip 430 configured to mate to the first arm by attaching to the set of grooves on the proximal end of the first arm. The tip holds the soft tissue fixation device 100 in place as the device is positioned, to or through the aperture in the cortical bone, and secured. The soft tissue fixation device may be further secured to the applicator via sutures 435 that pass through the tunnel 155 on the device and attach to the handle of the applicator. This mechanism of securing the device to the applicator not only maintains the device in the optimal orientation, but further provides a counter-force to the driver and screw, or other tool or tools (including non-threaded) as the case may be, that cause the device to open proximally toward the engaged position.

The cannulated shaft further encloses a driver (not shown) passing within the shaft and connected to the knob 420 for applying a torque to the screw inserted into the threaded socket of the first arm (as described in reference to FIG. 2). The knob 420 is proximal to the applicator handle 415. The driver includes a driver head at the distal end of the applicator. The driver head may be one of several types, including but not limited to a Phillips head, a flat head, a hex key head, a torx head, or even a custom head that is matable to a custom screw back. The driver serves to transfer an application of torque force from the knob to the screw to advance the screw into the first arm, thereby causing the soft tissue fixation device to proceed into an engaged position. The driver is securely enclosed within the shaft of the applicator 410, and free to rotate to provide the driving force to the screw.

The cannulated shaft may further serve as an extension with a small cross-sectional size to facilitate procedures that require maneuvering into small spaces and to reach target areas, such as during arthroscopic surgery. By having a low profile, the cannulated shaft provides for minimally invasive procedures when inserting the soft tissue fixation device.

Figure 5A:
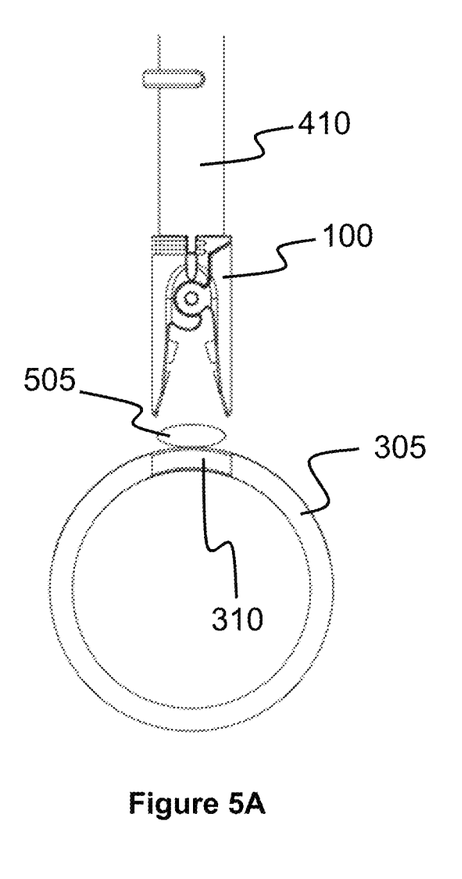
FIGS. 5A-5C illustrate an example of the insertion and securing of the implantable soft tissue fixation device in an aperture.
Figure 5B:
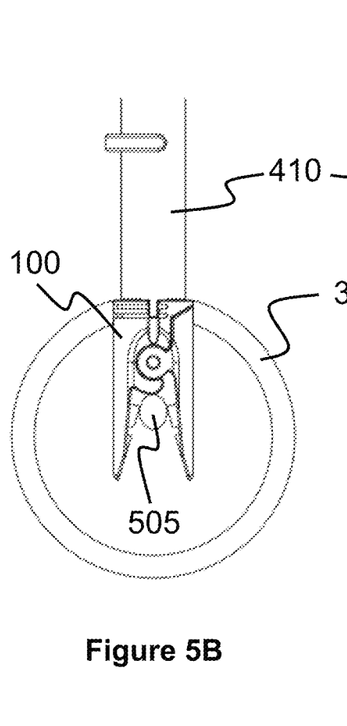
Figure 5C:
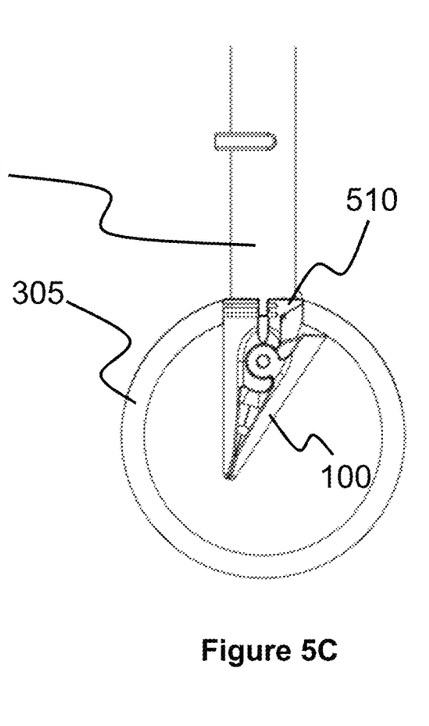

FIGS. 5A-5C illustrate an example of an insertion and securing of the implantable soft tissue fixation device in an aperture. FIG. 5A shows an example of soft tissue 505 extended across an aperture 310 in a cortical bone 305 structure. The soft tissue fixation device 100 is positioned by the applicator 410 over the soft tissue in line with the aperture, with the first arm of the device located on one side of the soft tissue, and the second arm of the device located on an opposite side of the soft tissue.

In FIG. 5B, the soft tissue fixation device 100 is advanced into the aperture 310 with the soft tissue 505 interposed between the first and second arms. As the device is inserted through the aperture, the soft tissue is interposed between the arms of the device, and thus transported through the aperture along with the device. In some instances, the soft tissue fixation device may not need to be wholly inserted through the cortical bone before being advanced to an engaged position. For example, the device may be engaged when the proximal ends (proximal to the hinge center of rotation) of the first and second arms are flush, or even proud, relative to the surface of the cortical bone aperture. In some embodiments, the screw of the device may be advanced while the device is being inserted into its final desired position and location. However, it may be preferable to advance the screw either after the device is through the cortical bone completely, or after the device is placed flush or proud, relative to the surface of the aperture cortical bone.

In some embodiments, the soft tissue fixation device comprises a lip 510 on the proximal end of the first arm adjacent to the proximal end of the second arm. This lip 510 can provide a mechanical stopper to prevent the soft tissue fixation device from being inserted into the aperture beyond a certain depth. For example, if the lip of the soft tissue fixation device comprises a profile such that it extends beyond the superficial surface rim of the aperture (not depicted) while the device is in an engaged position, then the soft tissue fixation device may only be inserted to the point where the lip prevents further insertion. Notably, a notch cutout on the outer surface of the proximal aspect of the second arm could also create a relative lip of device material that overhangs the edge of cortical bone on the surface of an aperture when the device is in an engaged position. Also, a protrusion of device material creating a relative ridge on the outer surface of the proximal aspect of the second arm could create the same effect as a relative lip of device material created from a notch cutout.

FIG. 5C provides an example of a fully inserted and subsequently engaged soft tissue fixation device. Once the soft tissue fixation device passes to a desired depth, the operator may advance, or initiate the advancement, as the case may be, of the screw into the threaded socket to cause the soft tissue fixation device to transition completely to an engaged position. In the engaged position, the first jaw on the distal end of the first arm and the second jaw on the distal end of the second arm compress and hold the soft tissue. In some embodiments, sutures may be applied to the soft tissue fixation device to further secure the device in an engaged position, as described in FIG. 3 above. Also, as described above, the sutures alone may create and maintain the engaged position of the device, with or without the screw mechanism.

Once the soft tissue fixation device captures soft tissue and if it then is placed below cortical bone in a fully engaged position, a larger profile created by the proximal ends of the device will prevent the device from backing out through the aperture in the cortical bone, as shown in FIG. 3 and FIG. 5C. Additionally, the proximal end of at least one of the first arm and second arm will provide an anchor against a backside of the cortical bone. The soft tissue would thus be engaged and fixated to bone. The anchoring force on the proximal ends of the first and second arms against the backside of the aperture can be provided by any elastic tension of the soft tissue held by the soft tissue fixation device. For example, if a muscle connected to the soft tissue contracts, the muscle will cause an elastic tension, or pull, on the soft tissue, thereby causing the soft tissue fixation device to anchor or self-reinforce against the backside of the cortical bone. With this anchoring, the motor abilities associated with the muscle may be optimally restored, as the device will allow the muscle to once again be attached to bone.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be achieved with devices of forms that deviate from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. For example, the insertion of the soft tissue fixation device may be done concurrently with the advancement of the screw into the first arm such that a gripping force is exerted on the soft tissue as the device is being inserted. The accompanying method claims present elements of the various steps in a sample order, and are not meant to be limited to the specific order or hierarchy presented.

Terms such as "top," "upper," "bottom," "lower," "right," "left," "up," "down," "forward," "backward," and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as an "aspect" may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such as an "embodiment" may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as a "configuration" may refer to one or more configurations and vice versa.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology.

What is claimed is:

1. An apparatus for affixing soft tissue to bone, the apparatus comprising:
   a first arm comprising a first jaw on a distal end of the first arm and a threaded socket for insertion of a screw; and
   a second arm mated to the first arm at a hinge that provides a single pivot point, the second arm comprising a second jaw on a distal end of the second arm, and the hinge being located between the proximal ends of the first and second arms and distal ends of the first and second arms,
   wherein, to enter the apparatus into an engaged position, the second arm pivots in reference to the first arm around the single pivot point provided by the hinge such that the distal end of the second arm closes towards the distal end of the first arm, and the proximal end of the second arm moves away from the proximal end of the first arm, the engaged position causing the first jaw on the distal end of the first arm and the second jaw on the distal end of the second arm to compress and hold soft tissue, and
   wherein the screw, when advanced into the threaded socket towards the distal end of the first arm, applies a force from a distal end of the screw in direct contact with the second arm to cause the second arm to progressively pivot in reference to the first arm around the single pivot point provided by the hinge to advance the apparatus into the engaged position.

2. The apparatus of claim 1, wherein an outer surface of the first arm is substantially parallel to an outer surface of the second arm in an unengaged position, arid wherein the outer surface of the first arm is at an angle to the outer surface of the second arm in an engaged position.

3. The apparatus of claim 2, wherein the first and second arms have a smaller insertion profile in the unengaged position when compared to the first and second arms in the engaged position.

4. The apparatus of claim 2, wherein, when the apparatus is entered into the engaged position after full insertion through an aperture created through a surface of bone in the unengaged position, the proximal ends of the first arm and second arm, having a larger dimension than the aperture when in the engaged position, provide an anchor against a backside of the aperture in the bone.

5. The apparatus of claim 2, wherein, when the apparatus is advanced towards the engaged position after partial insertion into an aperture created through a surface of bone in the unengaged position, the first arm and second arm provide at least one of an anchor or fixation against a side of the aperture in the bone.

6. The apparatus of claim 1, wherein each of the first and second arms comprises a set of channels through which sutures can pass, wherein the first and second arms are securable in the engaged position by securing sutures passing through the sets of channels to one another.

7. The apparatus of claim 1, wherein the screw is configured to secure sutures to the first arm, the screw securing the sutures by compressing the sutures against the threaded socket when the screw is advanced.

8. The apparatus of claim 1, wherein at least one of the first jaw and the second jaw comprises at least one of a set of horizontal teeth and a set of vertical teeth.

9. The apparatus of claim 1, wherein at least one of the first and second arms comprises one or more sets of ridges at the proximal end, the one or more sets of ridges running circumferentially along the outer surface of the at least one of the first and second arms.

10. The apparatus of claim 1, wherein the first arm further comprises a set of mating grooves on the proximal end of the first arm.

11. The apparatus of claim 10, wherein the set of mating groves on the proximal end of the first arm is attachable to a tip of an applicator.

12. The apparatus of claim 1, wherein the hinge comprises a tunnel passing from one side of the hinge through to the opposite side of the hinge.

\* \* \* \* \*